United States Patent [19]

Bonaldi et al.

[11] Patent Number: 5,117,017
[45] Date of Patent: May 26, 1992

[54] PROCESS FOR PREPARING HIGH PURITY 3-α-7-β-DIHYDROXYCHOLANIC ACID

[75] Inventors: Antonio Bonaldi, Chiuduno; Egidio Molinari, Longone del Segrino, both of Italy

[73] Assignee: Erregierre Industria Chimica S.p.A., San Paolo d'Argon, Italy

[21] Appl. No.: 758,513

[22] Filed: Sep. 6, 1991

Related U.S. Application Data

[63] Continuation of Ser. No. 483,729, Feb. 23, 1990, abandoned.

[30] Foreign Application Priority Data

Mar. 6, 1989 [IT] Italy ................. 19666 A/89

[51] Int. Cl.$^5$ ............................. C07J 75/00
[52] U.S. Cl. ................................. 552/553
[58] Field of Search ........................ 552/553

[56] References Cited

FOREIGN PATENT DOCUMENTS 1081929 9/1967 United Kingdom ............. 552/544

OTHER PUBLICATIONS

Foye, Principals of Medicinal Chemistry (Philadelphia, Lea and Febiger 1981) p. 503.

Primary Examiner—Marianne Cintins
Assistant Examiner—Kimberly J. Kestler
Attorney, Agent, or Firm—Birch, Stewart, Kolasch & Birch

[57] ABSTRACT

A process for preparing 3-α-7-β-dihydroxycholanic acid from a crude product containing up to 15% by weight of 3-α-7-α-dihydroxycholanic acid and up to 1% by weight of 3α-hydroxycholanic acid, by esterifying with methanol, crystallizing from a mixture of solvents consisting of methanol, an aromatic solvent and water and recrystallizing from a mixture of methanol, aromatic solvent and water.

10 Claims, No Drawings

PROCESS FOR PREPARING HIGH PURITY 3-α-7-β-DIHYDROXYCHOLANIC ACID

This application is a continuation of application Ser. No. 07/483,729 filed on Feb. 23, 1990, now abandoned.

PRIOR ART 3-alpha-7-beta-dihydroxycholanic acid is a product of considerable interest in human therapy, in which it is used for many functions such as solubilizing biliary calculi, reducing the percentages of cholesterol in the blood, reducing glycemia, as a diuretic and as a lipid metabolism accelerator.

Various processes are known for preparing 3-alpha-7-beta-dihydroxycholanic acid. All these processes have the drawback of producing a mixture of 3-alpha-7-beta-dihydroxycholanic acid and by-products such as 3-alpha-7-beta-dihydroxycholanic acid and 3-alpha-hydroxycholanic acid, which are difficult to separate.

All processes for separating the components of said mixture which have been proposed up to the present time have proved industrially costly and of limited efficiency.

SUMMARY OF THE INVENTION

We have now discovered a new process which enables high purity 3-alpha-7-beta-dihydroxycholanic acid to be obtained from a crude product containing up to 15% by weight of 3-alpha-7-beta-dihydroxycholanic acid and up to 1% by weight of 3-alpha-7-beta-dihydroxycholanic acid.

Said process is characterised by:

a) esterifying the crude product with methanol in the presence of an acid catalyst;

b) crystallizing the obtaining 3-alpha-7-beta-dihydroxycholanic methyl ester from an aromatic solvent;

c) recrystallizing the methylester from a mixture of methanol, aromatic solvent and water;

d) subjecting the recrystallized methylester to alkaline hydrolysis in a hydroalcoholic environment to obtain pure 3-alpha-7-beta-dihydroxycholanic acid.

DETAILED DESCRIPTION OF THE INVENTION

The characteristics and advantages of the process for obtaining high purity 3-alpha-7-beta-dihydroxycholanic acid according to the present invention will be more apparent from the following detailed description.

The starting product used is a 3-alpha-7-beta-dihydroxycholanic crude acid containing 10-15% by weight of 3-alpha-7-beta-dihydroxycholanic acid and about 1% by weight of 3-alpha-7-beta-dihydroxycholanic acid, as is obtained by known preparation methods.

This product is treated with an excess of methanol in the presence of an acid catalyst at boiling point under reflux for 5-10 hours. The weight ratio of methanol to crude acid is between 1:1 and 10:1. The catalyst used can be sulphuric acid, methanesulphonic acid or para-toluenesulphonic acid in a quantity of between 2% and 4% by weight of the crude product.

On termination of treatment the methanol is distilled off until the weight ratio of methanol to crude produce is 1:1. A quantity of benzene or toluene or xylene varying from 4 to 6 times the initial crude product is then added, after which an equal quantity of water is added.

The mixture is boiled under reflux for 20–40 minutes and then cooled to between 0° C. and 5° C. to crystallize the pure 3-alpha-7-beta-dihydroxycholanic methyl ester (the esters of the other acids contained in the starting product do not crystallize).

The crystallized product is filtered off, washed with an aromatic solvent, redissolved under hot conditions in a mixture of methanol and aromatic solvent, e.g. benzene, toluene or xylene, water is added and the product is recrystallized by cooling to 0° C.

The recrystallized product is filtered off and washed with solvent, and then subjected to alkaline hydrolysis by means of a mixture of methanol or other water-soluble alcohol, and 30% sodium hydroxide in water by boiling under reflux for 1-3 hours.

The methanol is distilled off, the residue taken up in water, the pH adjusted to 7-8, ethyl acetate is added and the mixture acidified to pH 3, after which the product is crystallized by cooling to between 0° C. and 5° C., filtered off and washed firstly with water and then with ethyl acetate.

The product is dried at 80° C. to obtain 3-alpha-7-beta-dihydroxycholanic acid free of 3-alpha-dihydroxycholanic acid and containing less than 0.5% of 3-alpha-7-alpha-dihydroxycholanic acid.

The following examples of the preparation of high purity 3-alpha-7-beta-dihydroxycholanic acid are given for the purposes of non-limiting illustration.

EXAMPLE 1

100 g of crude 3-alpha-7-beta-dihydroxycholanic acid (containing 15% of 3-alpha-7-alpha-dihydroxycholanic acid and 1% of 3-alpha-hydroxycholanic acid) are treated under boiling conditions with 500 g of methanol and 3 g of sulphuric acid for 6 hours.

The methanol is then distilled off until the weight ratio of methanol to crude product is 1:1. The residue is taken up in 500 g of benzene and 500 g of water. The mixture is heated for 30 minutes under reflux and is then cooled to 0° C. and filtered, the product then being washed with benzene.

The wet product is recrystallized by being dissolved under hot conditions in 100 g of methanol and 500 g of benzene. 500 g of water are then added, the mixture is cooled to 0° C. and filtered, and the product is washed with benzene.

The pure ester obtained in this manner is treated with 100 g of methanol and 300 g of 30% sodium hydroxide, with heating under reflux for 2 hours.

The methanol is finally distilled off, the residue taken up in water, and the pH adjusted to 7-8 with 30% sulphuric acid. 200 g of ethyl acetate are added and the pH is adjusted to 3 with 30% sulphuric acid.

The mixture is cooled to 0° C. and filtered, and the product is washed well with water and then with ethyl acetate.

It is dried at 80° C. to obtain 74 g of pure 3-alpha-7-beta-dihydroxycholanic acid.

- The 3-alpha-7-beta-dihydroxycholanic acid content is less than 0.5%.

3-alpha-hydroxycholanic acid is absent.

EXAMPLE 2

Example 1 repeated using toluene instead of benzene. 76 g of product are obtained having the same characteristics as Example 1.

We claim:

1. A process for preparing high purity 3-α-7-β-dihydroxycholanic acid from a crude product containing up to 15% by weight of 3-α-7-α-dihydroxycholanic acid and up to 1% by weight of 3-α-hydroxycholanic acid, comprising:
a) esterifying the crude product with excess methanol in the presence of an acid catalyst;
b) crystallizing the obtained 3-α-7-β-dihydrocholanic methyl ester from a mixture of solvents consisting of the same methanol contained in the reaction mixture coming from step a), an aromatic solvent, and water;
c) recrystallizing the methylester of step b) from a mixture of methanol, aromatic solvent and water; and
d) subjecting the recrystallized methylester to alkaline hydrolysis in a hydroalcoholic environment to obtain pure 3-α-7-β-dihydroxycholanic acid.

2. The process as claimed in claim 1, wherein said esterification is conducted by boiling under reflux.

3. The process as claimed in claim 1, wherein the weight ratio of methanol to crude product used in step a) is between 1:1 and 10:1.

4. The process as claimed in claim 1, wherein said acid catalyst is selected from the group consisting of sulphuric acid, methanesulphonic acid, and paratoluenesulphonic acid.

5. The process as claimed in claim 1, wherein said acid catalyst is selected from the group consisting of sulphuric acid, methanesulphonic acid, and paratoluenesulphonic acid, said acid being used in a quantity of between 2% and 4% by weight of the crude product.

6. The process as claimed in claim 1, wherein before carrying out the crystallization of step b), methanol is partially distilled off until the weight ratio of methanol to crude product is 1:1.

7. The process as claimed in claim 1, wherein in the crystallization step b) the aromatic solvent is selected from the group consisting of benzene toluene and xylene, and wherein the amount of aromatic solvent varies from 4 to 6 times the initial crude product weight and to which an equal amount of water is added.

8. The process as claimed in claim 1, wherein said recrystallization is conducted in a mixture of methanol, water, and an aromatic solvent selected from the group consisting of benzene, toluene, and xylene and water.

9. The process as claimed in claim 1, wherein said alkaline hydrolysis is conducted with a mixture of methanol, or other water-soluble alcohol, and 30% sodium hydroxide in water.

10. The process as claimed in claim 1, wherein said alkaline hydrolysis is conducted by boiling under reflux for 1–3 hours.

* * * * *